US006830728B2

United States Patent
Nguyen et al.

(10) Patent No.: US 6,830,728 B2
(45) Date of Patent: Dec. 14, 2004

(54) DEVICE AND METHOD FOR PNEUMATIC GAS SAMPLING FOR GAS SENSORS

(75) Inventors: Viet Nguyen, Gaithersburg, MD (US); Russell Chung, Springfield, VA (US); Robert A. McGill, Lorton, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 483 days.

(21) Appl. No.: 09/893,016

(22) Filed: Jun. 28, 2001

(65) Prior Publication Data

US 2002/0016004 A1 Feb. 7, 2002

Related U.S. Application Data

(60) Provisional application No. 60/214,788, filed on Jun. 28, 2000.

(51) Int. Cl.[7] ............................................. G01N 31/00
(52) U.S. Cl. ........................ 422/52; 422/83; 422/86; 422/88; 422/93
(58) Field of Search ............................ 422/83–93, 52

(56) References Cited

U.S. PATENT DOCUMENTS 3,847,552 A * 11/1974 Hobgood et al. ............. 436/26

* cited by examiner

*Primary Examiner*—Jill Warden
*Assistant Examiner*—Sam P. Siefke
(74) *Attorney, Agent, or Firm*—John J. Karasek; George A. Kap

(57) ABSTRACT

Apparatus and method for detecting presence of an analyte in ambient air. The apparatus comprising a valve for admitting ambient air, a line for conveying the air to a sensing element, a housing for isolating the environment around the sensing element, an inlet port for flowing the air tho the sensing element in a turbulent flow in a direction substantially perpendicularly to the sensing element, an outlet port for conveying the air from the sensing element, and a pump in communication with the outlet port for providing suction for drawing the air to the sensing element. The method includes the steps of drawing in ambient air that may contain an analyte, projecting the air at a sensing element in a turbulent flow by flowing the air at the sensing element, the sensing element having on its surface a chemoselective material that selectively interacts with the analyte, and detecting the interaction of the analyte with the sensing element.

11 Claims, 4 Drawing Sheets

DEVICE AND METHOD FOR PNEUMATIC GAS SAMPLING FOR GAS SENSORS

REFERENCE TO RELATED APPLICATION

This is a non-provisional patent application of provisional application Ser. No. 60/214,788 filed Jun. 28, 2000, and entitled "Device and Method for Pneumatic Gas Sampling for Gas Sensors" wherein the inventors are Viet Khanh Nguyen, Russell Chung and Robert Andrew McGill, the filing dated of which is hereby claimed.

BACKGROUND OF THE INVENTION

1. Field of the Invention

The invention relates generally to a method and device for detecting analytes in ambient air and specifically to a method and device for accelerating chemical sensor kinetics and for restoring a baseline for a chemical sensor.

2. Description of the Related Art

Ambient air sampling for chemical sensor applications can take a variety of forms that can broadly be separated into two classes, passive and active sampling. In passive sampling, the ambient gas is exposed to the sensor without active pumping from a pump that is integral to the sensor or detector. The sensor can be exposed directly to the ambient air with or without a membrane that serves to prevent contamination of the sensor. Signal kinetics are relatively slow and are largely controlled by diffusion and the thickness of the polymer coated sensor. No accommodation for signal baseline restoration is incorporated in a passive sampling mode, and if the device suffers from baseline drift due to for example humidity or temperature changes, the signal contribution from an analyte exposure will become uncertain under dynamically changing environmental conditions. Active sampling allows active flow of the air sample and can direct the flow through pneumatic tubing, valve(s), collection devices, and gas chromatographic columns prior to or down stream of the sensor. Active sampling draws sample past the polymer coated sensor, but does little to accelerate the sorption or desorption of the analyte molecules from the active surface of a chemical sensor.

BRIEF SUMMARY OF THE INVENTION

Accordingly, it is an object of the present invention to provide a method and apparatus for delivering a sample of ambient air/gas to a chemical sensor resulting in accelerated signal kinetics.

It is a further object of the present invention to provide a method and apparatus for delivering a sample of ambient air to a chemical sensor wherein the interaction of molecules of an analyte in the gas sample with the surface of the sensor is maximized.

It is a further object of the present invention to provide a method and apparatus for delivering a sample of ambient air to a chemical sensor whereby the interaction of interfering molecules, such as water in the gas sample, with the surface of the chemical sensor can be minimized.

It is a further object of the present invention to provide a method and apparatus for delivering samples of ambient air to a chemical sensor whereby a baseline for the chemical sensor can be established between discrete samples.

It is a further object of the present invention to provide a pulsed gas sampling technique that increases the sorption rate of analyte into a sorbent coated chemical sensor by up to 3 orders of magnitude faster than conventional pneumatic gas sampling techniques that pump air over a sorbent film at atmospheric pressure.

It is a further object of the present invention to provide a pulsed gas sampling technique that allows rapid clean up of a sorbent coated sensor to a vapor-free state that allows the identification of an essentially analyte-free baseline.

These and other objects are attained by an apparatus for detecting the presence of at least one analyte in ambient air, the apparatus comprising at least one sensing element comprising a surface having at least one sorbent coating, such as a chemoselective polymer coating, that selectively interacts with at least one analyte and provides a detector for detecting the selective interaction of the at least one chemoselective polymer with the analyte, a housing that encloses an environment surrounding the at least one sensing element, the housing including an inlet port connected to a sampling pump for taking a gaseous sample from ambient air into the housing under reduced pressure, a valve or something similar for sealing the environment surrounding the sensing element so that the environment surrounding the at least one sensing element can be isolated from ambient air and evacuated, and an outlet port connected to the sampling pump under vacuum for removing the gaseous sample from the environment surrounding the at least one sensing element, wherein the size and orientation of the inlet port are selected so that the gaseous sample is directed to strike each at least one sensing element in a turbulent flow that is substantially perpendicular to the surface of the sensing element having the chemoselective polymer.

These and other objects are further attained by a method of monitoring ambient air to detect the presence of an analyte, the method comprising the steps of (a) providing an apparatus that comprises a sensing element comprising a surface having a sorbent polymer coating that selectively interacts with the analyte and means to detect the selective interaction of the sorbent coating with the analyte, a housing that encloses an environment surrounding the sensing element, the housing including an inlet port connected to a sampling pump for removing or collecting a gaseous sample from ambient air and taking the gaseous sample into the housing under pressure, wherein the size and orientation of the inlet port are selected so that the gaseous sample is directed to the sensing element in a turbulent flow that is substantially perpendicular to the surface having the sorbent coating, an outlet port for removing the gaseous sample from the environment surrounding the sensing element and means for sealing the environment surrounding the sensing element so that the environment surrounding the sensing element can be isolated from ambient air and evacuated, (b) sealing the environment surrounding the sensing element from ambient air and evacuating the environment, so that a baseline for the sensing element is established, (c) collecting a gaseous sample from ambient air and taking the gaseous sample into the housing initially under reduced pressure so that the gaseous sample is directed to strike the sensing element in a turbulent flow that is substantially perpendicular to the surface having the chemoselective polymer coating, whereby molecules of the analyte, if present in the gaseous sample, interact with the chemoselective polymer and wherein any such interaction is detected, and whereby low molecular weight species not of interest in the gaseous sample are propelled by the turbulent flow towards the outlet port, and (d) repeating steps (b)–(c)

to cyclically monitor the ambient gas for the presence of the analyte and restore the sensing element to its baseline.

DETAILED DESCRIPTION OF THE PREFERRED EMBODIMENT

Figure 1:
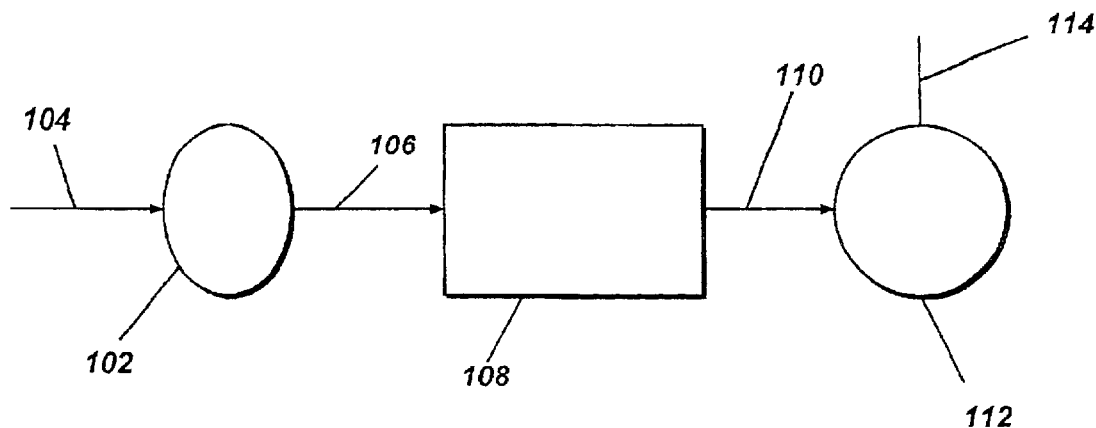
FIG. 1 is a sketch of the first embodiment of the invention illustrating the evacuated gas sampling pneumatic system, or the basic embodiment, which has fast signal rise kinetics and a relatively slow recovery time.

This invention provides a generic gas sampling technique for chemical sensors such, as the chemoselective polymer coated surface acoustic wave (SAW) devices, that allows for rapid equilibrated chemical sensor signal responses and recovery to baseline kinetics for relatively low volatility vapors such as chemical nerve and blister agents in the 1–2 second time domain or less. In addition, this invention allows a simple and rapid environmentally independent signal baseline restoration in less than about 2 seconds after vapor exposure, without the need for any consumable materials.

A pulsed pneumatic gas sampling technique of this invention reduces the sorption of water into polar polymers by up to 95%. One hypothesis of the mechanism is as follows: the water molecules have a molecular size that is comparable to oxygen and nitrogen molecules in the air and in a turbulent pneumatic flow path, the molecules become entrained in the air flow and are significantly prevented from sorbing to the polymer film that they flow past. Larger molecules of interest are less affected by the turbulent flow path and are readily sorbed to thin polymer films.

The apparatus of this invention can be used with any type of chemical sensor, including but not limited to a surface acoustic wave sensor (SAW), that has a chemoselective surface, that is, a sorbent coated or functionalized surface that selectively interacts with an analyte. Moreover, the invention is intended to include multiple sensors or arrays of sensors or sensors with surfaces having multiple coatings for detecting multiple analytes. Multiple sensors may share a common sampling pump and a common vacuum pump, but may have separate chambers with separate inlet ports and outlet ports. In one such design, a sample of ambient air is pumped into a cubic structure having a chemical sensor on each of four faces of the cube, each sensor sharing a common sampling pump and vacuum pump, but having its own separate inlet and outlet.

In the apparatus of the invention, the surface of the chemical sensing element is enclosed or surrounded by a manifold or housing that allows the surface to be sealed off from the ambient environment and for the area surrounding the surface to be evacuated. Evacuation of the chamber surrounding the surface of the chemical sensing element removes volatile elements from the sorbent coating and the area surrounding it and allows for a baseline for the sensing element to be established. A pressure on the order of 10"–17" mercury will substantially remove or clean the surface of the sensing element where the element is 0.3"×0.05", the inlet port is 0.1" directly below the tubular inlet port of 0.4" in diameter with the pump flow at 3 l/min. Evacuation to reduced pressure also increases the sorbency characteristics of the chemoselective polymer by removing any volatile molecules from the interior of the polymer. The housing includes an inlet port that is connected to a pump so that a gas sample taken from ambient air can be pumped into the chamber. The gas sample entering the chamber attains a high velocity and a turbulent flow due to the action of the pump and due to the release of the vacuum. The turbulent flow is directed by the placement of the inlet port relative to the surface of the sensing element so the gas sample strikes the surface of the sensing element in a substantially perpendicular manner with respect to the surface of the sensing element, as opposed to being directed in a substantially parallel direction to the surface. This dramatically increases the opportunity for and speed of interaction of any analytes of the gas sample with the surface of the sensing element. (The force of the turbulent flow carries small molecules, such as water molecules, that could potentially interfere with the response of the chemoselective polymer, away from the sensing element so that their interaction with the chemoselective polymer is minimized.) As used herein, "substantially perpendicular" means nonparallel or at an angle and that the overall flow vector for the turbulent gas flaw is perpendicular to the surface of the sensor element. Some deviation from perpendicular are acceptable.

After the gas sample has had sufficient time to interact with the chemoselective polymer so that molecules of the analyte, if present, can be detected, the inlet port is sealed off and the chamber surrounding the sensing element is evacuated to return the sensor to its baseline. The cycle is then repeated so that ambient air is monitored continuously over a period of time.

The interaction of an analyte with the chemoselective material of the sensing element generates a signal which can be monitored according to the type of sensing element.

Because of the faster signal kinetics, time of the sensing element of the present invention compared to conventional chemical sensors, it is now possible to use a chemical detector that operates with an orthogonal technology to sorbent material based detector with similar signal kinetics. The data from each of the two sensors can be merged and analyzed together.

A chemical transducer with a chemical interface such as a polymer coated SAW sensor, is operated under alternating pressure conditions from ambient to evacuated in a repeated cycle. Exposing the sensor, initially under reduced pressure, to ambient air rapidly draws analyte vapor into the sensor, accelerating and driving vapor molecules into the polymer film coated on top of the SAW device. The SAW sensor frequency signal is monitored during the cyclical operations. Exposure to an uncalibrated nerve agent simulant dimethylmethylphosphonate (DMMP) vapor source for approximately 0.5 seconds, during the sensor exposure to ambient air results in a rapid response providing 90% of the total signal response within approximately 0.2 seconds. After the vapor source is removed, the signal recovery is accelerated by sweeping out relatively volatile vapors with a flow through purging step. Immediately following the flow through purging, the evacuation is applied first to remove the volatile species and then the flow through purging is used to remove the non-volatile species as they are "stickier" than the volatile species. An increase in signal response kinetics for chemical warfare agents of approximately 1–2 orders of magnitude can be established with the pressure modulated pneumatics.

Figure 3:
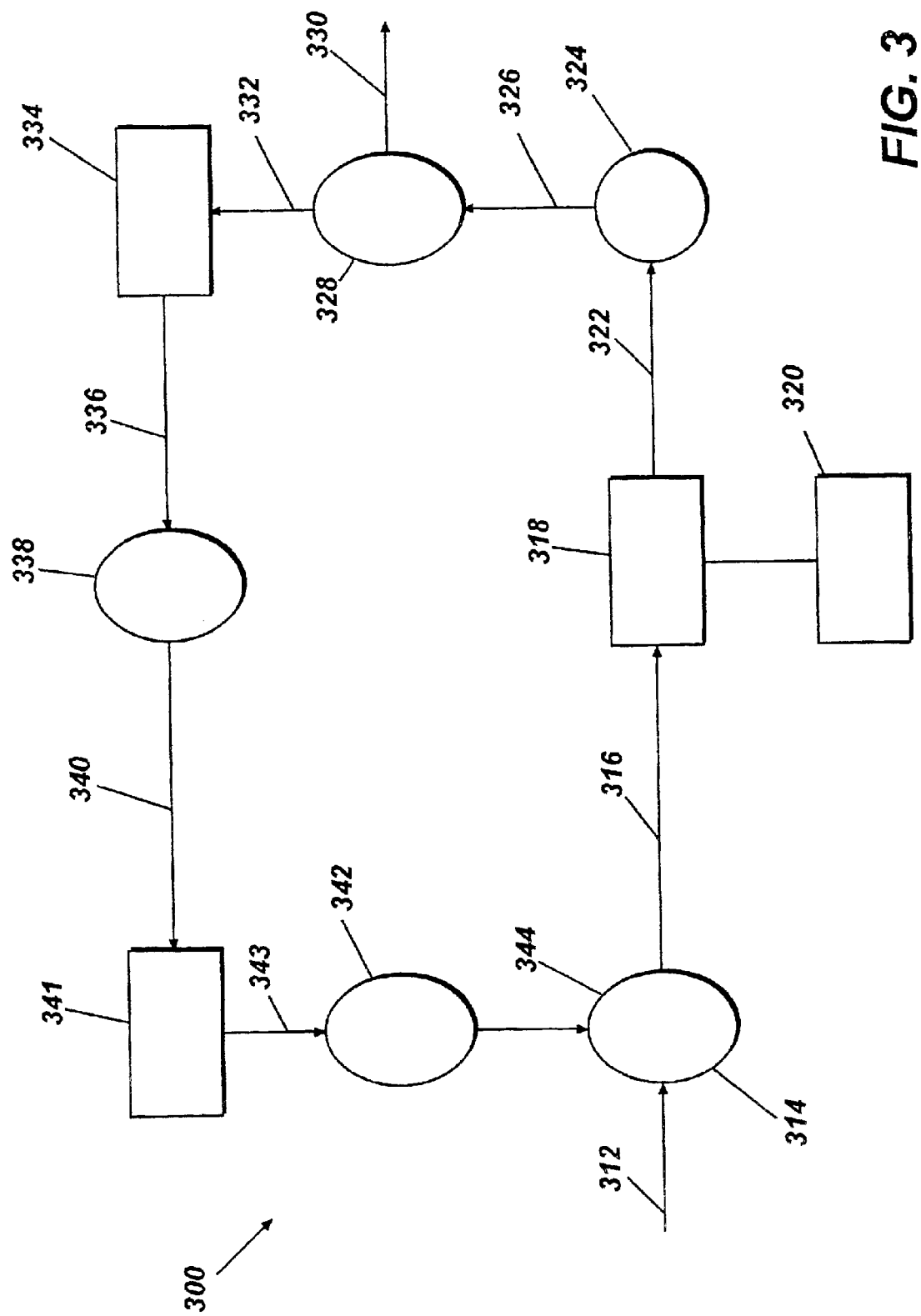
FIG. 3 is a sketch of the second embodiment of the invention illustrating the flush evacuated gas sampling pneumatic system, or the flush embodiment, which results in rapid signal kinetics during and after vapor exposure.
Figure 4:
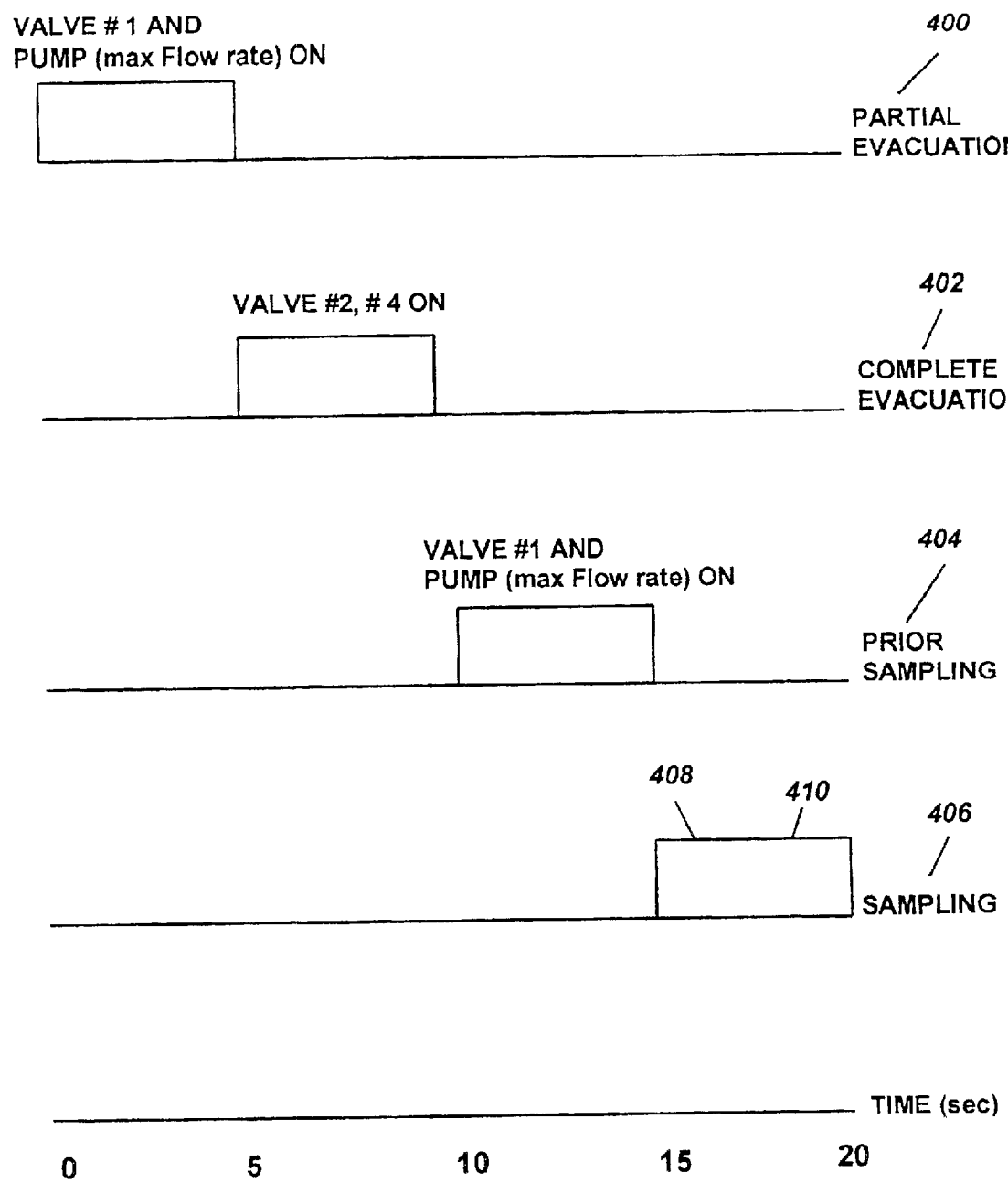
FIG. 4 is a sampling/detect timing diagram of the flush embodiment of FIG. 3.
Figure 5:
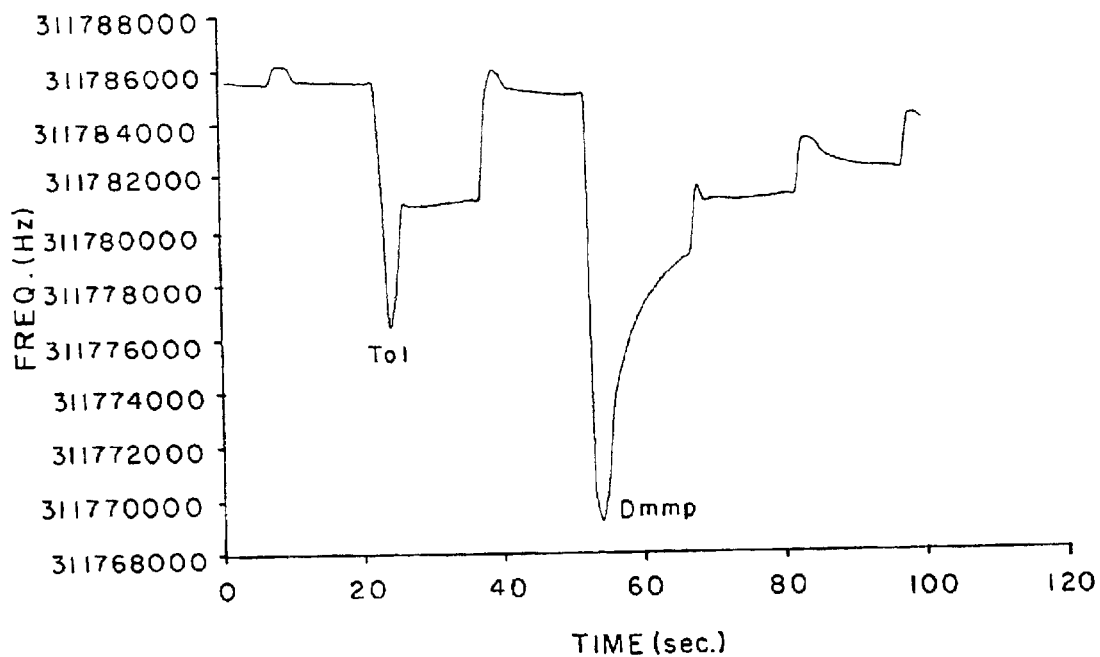
FIG. 5 is a plot for a SAW sensor response showing fast signal response and relatively slow recovery kinetics by incorporating modulated pneumatics of the FIG. 1 basic embodiment.
Figure 6:
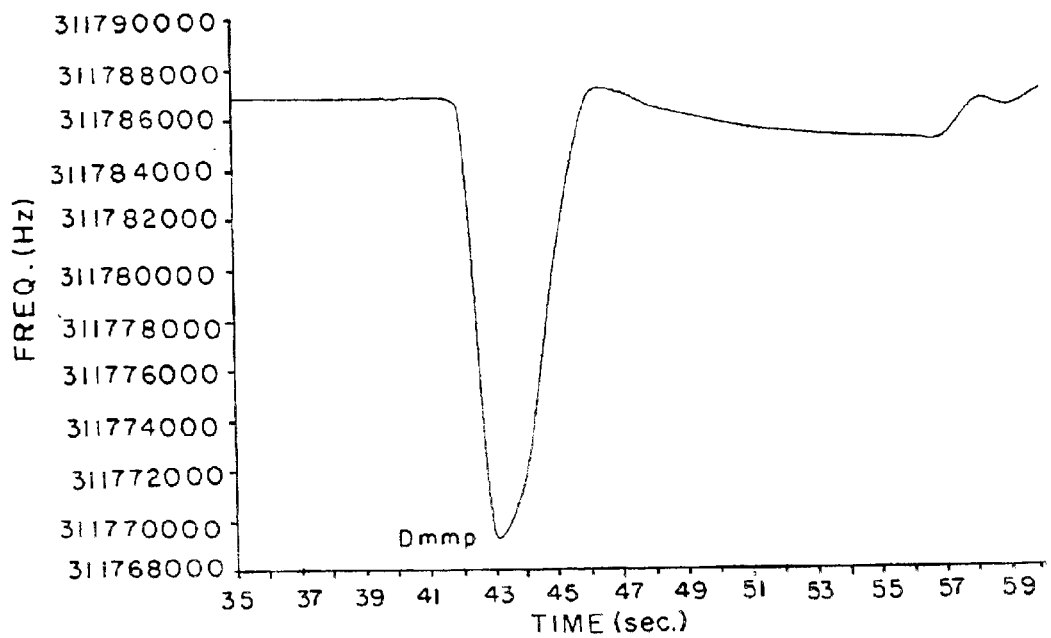
FIG. 6 is a plot for a SAW sensor response showing fast signal response and recovery kinetics by incorporating pressure modulated pneumatics and flow through purging for the FIG. 3 flush embodiment.

In order to optimize the signal response and recovery kinetics, a pneumatic configuration shown in FIG. 3 was designed, with a timing diagram shown in FIG. 4. Recovery time of the FIG. 3 flush embodiment as compared to the FIG. 1 basic embodiment is greater than about 4 times, i.e., recovery time for the basic embodiment shown in FIG. 1 is typically 3–5 seconds and that for the FIG. 3 flush embodiment is typically less than 1 second. The cause and effect of various events during a typical cycle with the flush embodiment shown in FIG. 3 is illustrated in FIG. 4. Data collected for a DMMP exposure to a SAW sensor coated with a chemoselective polymer (NRL polymer AD1) is shown in FIGS. 5 and 6 for pneumatics with and without the purge flow through prior to applying evacuation. The rapid signal recovery kinetics observed with the application of flow through purging prior to evacuation is exemplified in FIG. 6 for the flush embodiment shown in FIG. 3. Signal response to 90% of the maximum signal is approximately 1 second as before, and the signal recovery to baseline is dramatically reduced to approximately 2 seconds for DMMP, a precursor for nerve agent manufacture and a nerve agent simulant.

Referring to the drawings, FIG. 1 is a sketch of the basic embodiment 100 of the invention. This basic embodiment includes 2-way valve 102 through which a gas sample of the ambient air is introduced through line 104; and then through line 106; through sensor housing 108 having inlet port, outlet port and a sensing element; through line 110; into pump 112; and out through exhaust line 114. The pump provides the suction to draw in the gas sample from the ambient air.

Figure 2:
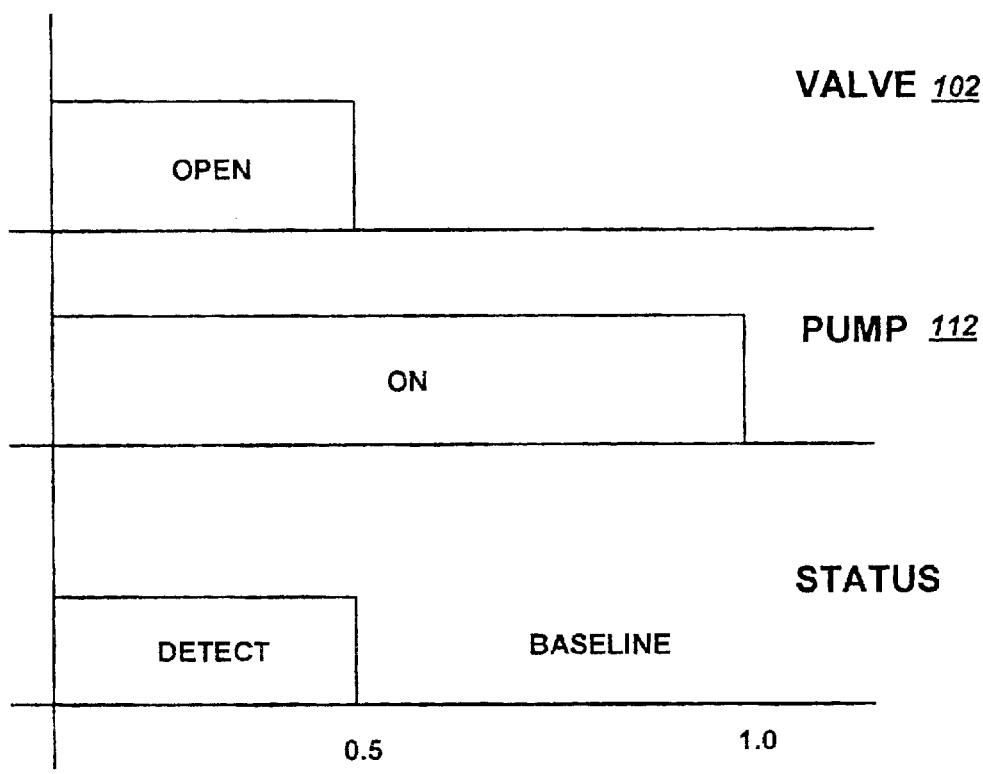
FIG. 2 is a gas sampling/detect timing diagram for the basic embodiment of FIG. 1.

Operation of the basic embodiment of FIG. 1 can be more easily described by reference to the timing diagram depicted in FIG. 2 which shows one period, duration of which can vary depending on the many variables of the system. As FIG. 2 shows, pump 112 is on during the entire period and draws in the gaseous sample during the time valve 102 is open. Detection of the analyte by the sensing element is also made during this time.

The time period required for identifying a clean baseline varies in time length depending on pumping properties and exact pneumatic configuration. For embodiments of FIGS. 1 and 3, the time typically varies between about 0.05 to 11 seconds.

FIG. 3 is a sketch of the flush embodiment of the sensor system 300 which draws in a gaseous sample of the ambient air through line 312. The ambient air can contain an analyte or gas which is desired to be removed. The ambient air can contain more than one analyte. The sample proceeds through 3-way valve 314 which then proceeds through line 316 to sensor housing 318 which contains an inlet port, an outlet port and one or more sensing elements which have a chemoselective material thereon. There may be more than one sensing element each covered with a different chemoselective material which interacts with different analytes or there can be a single sensing element coated with one or more different chemoselective materials for detecting presence of different analytes. Neither the sensing element nor the inlet or outlet ports are shown. The inlet port is arranged so that it delivers the sample in a turbulent flow that is directed at an angle or is substantially perpendicular to the sensing element.

A tubular inlet port 0.4" in ID with the sensing element spaced from the inlet by 0.1" at a flow rate of 3 l/min, can produce turbulent flow above the sensing element. Laminar flow can be obtained with the same arrangement but with inlet port at 0.5" ID.

From sensor housing 318 through exit port, the sample is conveyed through line 322 to pump 324. Pump 324 provides some impetus for drawing the sample against the sensing element. Pump 324 is adapted to convey gas through line 326 to 3-way valve 328 where the gas, or any part thereof, can be exhausted through line 330 or conveyed further through line 332 to scrubber 334. When moving through the scrubber, the air is stripped of analyte or cleaned and this scrubbed gas is used to restore the baseline condition by flowing it over the sensing element, as will be described.

After the gas is cleaned by stripping it in scrubber 334, it is conveyed through line 336 to 2-way valve 338, line 340, reservoir line 341, line 343, 2-way valve 342, line 344 and to valve 314.

Line 336, valve 338 and line 340, reservoir line 341, line 343, valve 342 and line 344 form a reservoir for scrubbed gas, which is typically the gas sample or any part thereof.

The flush embodiment of FIG. 3 is designed to restore baseline condition of the sensing element with the scrubbed gas, as is explained below.

Operation of the flush embodiment of FIG. 3 can be more easily understood by reference to FIG. 4, which is the timing diagram of the FIG. 3 embodiment. The cycle times given in FIG. 4 are merely illustrative and are not typical of the actual times. Referring to FIG. 4, partial evacuation cycle 400, i.e., the first cycle, is shown at the top and designates the cycle during which lines 312, 344 and 332 are closed off and pump 324 is on and exhausts all gases from valve 314, line 316, sensor housing 318 with its inlet and outlet ports and the sensing element, line 322, valve 328 and line 326 through exhaust line 330. As FIG. 4 indicates, duration of this cycle is 5 seconds and it provides a vacuum or low pressure, i.e., below atmospheric, over the sensing element. This condition can also be described as having valve 314 on and pump 324 also on, the pump providing the evacuation draw.

The next or the second cycle also has duration of 5 seconds and it is designated as complete evacuation or removal cycle 402 during which, lines 312 and 330 are closed and line 344 is opened so that gas can circulate in the closed system, with pump 324 on, through valve 314, line 316, sensor housing 318, line 322, line 326, valve 328, line 332, scrubber 334, line 336, valve 338, line 340, reservoir line 341, line 343, valve 342 and line 344, with line 312 being closed. The purpose of this cycle is to advance scrubbed reservoir gas against the sensing element in order to reset baseline condition thereof. This cycle results in a gas pressure over the sensing element that is higher than in the partial evacuation cycle but lower than atmospheric, assuming that the ambient air is at atmospheric pressure. At the commencement of this second cycle, since gas pressure over the sensing element is lower than that of the reservoir gas, this pressure differential is relied on to draw the reservoir gas in. As the reservoir gas, i.e., essentially from reservoir line 341, rushes in over the sensing element due to the pressure differential, it strips off analyte molecules from the sensing element to restore the sensing element to its baseline condition. This is made possible by the fact that the pressure over the sensing element is lower than the pressure of the reservoir gas thus creating a pressure differential for drawing in the reservoir gas. The other fact which makes possible restoration of the baseline condition is that the reservoir gas has been scrubbed of analyte. This cycle can also be described as the time both valve 314 and pump 328 are on. The second cycle can also be described as having valves 342 and 328 on.

The next or the third cycle is the sampling cycle 404, designated as prior sampling, during which line 312 is closed and line 332 is opened so that there is passage through valve 314; line 316; sensor housing 318 with inlet port, outlet port and the sensing element; line 322; pump 324; and out through line 330. The purpose of this third cycle, duration of which is 5 seconds, is to replenish the reservoir gas against the sensing element. As should be apparent, although the third cycle is designated as being prior sampling, no sampling of the ambient air is made.

The last or the fourth cycle 406, shown in FIG. 4, is designated as being sampling, and it does sample the ambient air. During this cycle, lines 344 and 332 are closed and line 312 is opened by virtue of manipulating valve 314 so that ambient air flows through line 312, valve 314, line 316, sensor housing 318, line 322, pump 324, line 326, valve 328, and out through line 330. The pressure differential between ambient air, which is typically atmospheric, and the pressure of the sensor housing, which is typically sub-atmospheric, provides partial impetus for drawing the ambient air in. The pressure differential is typically sufficient to draw in less than about one-half, and typically about one-third, of the gaseous sample that is tested, with remainder being drawn in by pump 328 which is turned on when the reservoir gas pressure and the pressure of the ambient air approximately equalize. In FIG. 4, portion of the ambient air that is drawn in by the pressure differential is denoted as 408 and the portion drawn in by pump 328 is denoted as 410.

Reservoir line 341 is typically ¼" ID and 5' long and the other lines are typically short and are ⅛"–¼" ID tubing. The reservoir section, which includes line 336, valve 338, line 340, reservoir line 341, line 343, line 342 and line 344, but essentially line 341 since volume of the other lines is small because they are typically short, acts as a reservoir of scrubbed gas for the system during the complete evacuation cycle when the scrubbed gas is introduced against the sensing element when the baseline condition of the sensing element is reestablished by removing analyte from the sensing element by the flowing scrubbed gas.

Because the baseline can be reset in a rapid fashion and in a repeated manner, if there are any environmental signal response drift issues, these can be readily nullified because the baseline can be reset in less than about two seconds. Hence, temperature and humidity sensor signal drift issues are effectively eliminated.

Also, because of the very fast signal kinetics, the polymer coated SAW sensors are now comparable in kinetics to a chemical detector based on an orthogonal technology, such as the ion mobility spectrometer (IMS), which uses a direct vapor inlet, and not a membrane, or generally, a fast signal kinetic chemical detector based on an orthogonal detection technology, such as the IMS. Joining the two technologies together is important since it is of no use if one sensor is much faster in terms of responding to a gas because the fusion of any data or any signal processing algorithm becomes complicated and the fast sensor has to wait for the slow sensor to catch up.

EXAMPLES

An array of four ~250 MHz SAW chemical sensors (each separately coated with a thickness of approximately 50 nm of the NRL polymers CSP2, T1, AD1, and EH1 corresponding to 250 KHz frequency shift before and after coating) were pneumatically connected in parallel configuration to a miniature TD-4×2NA Brailsfordpump, and miniature 2-way valve as shown in FIG. 1 The pneumatics were operated with a repeated cycle that incorporated two main operations. 1. The sensor was evacuated (valve closed) by operating the pump to reduce the pressure within the sensor chamber and thereby remove air, and vapors in the pneumatics contained between the pump, sensor, and valve. 2. Turning the pump off and switching the valve to the open position, to allow ambient air with an analyte dimethylmethylphosphonate (DMMP) vapor to rush into the pneumatics and the sensor array. Operations 1 & 2 were repeated in a continuous cycle, where operation 1 was maintained for a period of 5 seconds, and operation 2 was maintained for a period of 5 seconds. The cycle events are detailed in FIG. 2.

The following results were observed: exposing the sensor, initially under reduced pressure, to ambient air to rapidly draw analyte vapor into the sensor, accelerating and driving vapor molecules into the polymer film coated on top of the SAW device. The SAW sensor frequency signal was monitored during the cyclical operations 1 & 2 described above. Exposure to an uncalibrated DMMP vapor source for approximately 0.5 seconds, during operation 2, resulted in a rapid response providing 90% of the total signal response within approximately 0.2 of a second. The maximum responses were 35 KHz, 31 KHz, 26 KHz, and 6 KHz of signal for SAW devices coated with polymers EH1, T1, AD1, and CSP2 respectively. After the vapor source was removed, the signal recovery to baseline took an extended period of time of between 10 and 60 seconds, depending on the polymer. The corresponding signal response after 0.7 seconds from the identical SAW sensor coated with polymer EH1 and challenged with the same vapor challenge for "normal" vapor sampling (-continuous stream of the vapor pumped over the sensor at a constant pressure) produced a much slower signal response of 1000 Hz.

In order to improve the recovery of the SAW chemical sensor after vapor exposure, the evacuated stage was preceded by a continuous flow stream to remove volatile species from the sensor. Subsequent evacuation removed less volatile vapor components. This operation of baseline recovery allows a stepwise recovery to a clean vapor free baseline signal. In order to optimize the signal recovery kinetics, a redesigned pneumatic configuration was used as shown in FIG. 3, with a timing diagram shown in FIG. 4. Data collected for a DMMP exposure to a SAW sensor coated with NRL polymer Adiol is shown in FIGS. 5 and 6. The rapid signal recovery kinetics observed with the application of flow through purging prior to evacuation is exemplified in FIG. 6. Signal response to 90% of the maximum signal is approximately 1 second as before, and the signal recovery to baseline is dramatically reduced to approximately 2 seconds for dimethylmethylphosphonate (DMMP), a precursor to nerve agents and a nerve agent stimulant.

In addition to DMMP tests, toluene and dinitrotoluene exposure tests were carried out to evaluate the sampling technique for its effectiveness for more volatile and less volatile species. Responses to more volatile species, such as toluene, were reduced.

Obviously, many modifications and variations of the present invention are possible in light of the above teachings. It is therefore to be understood that, within the scope of the appended claims, the invention may be practiced otherwise than as specifically described.

What is claimed is:

1. An apparatus for detecting the presence of an analyte in ambient air, the apparatus comprising a sensing element comprising a surface having a coating of chemoselective material that selectively interacts with the analyte and means to detect the selective interaction of the chemoselective material with the analyte, a housing that encloses an environment surrounding the sensing element, the housing including an inlet port connected to a sampling pump for taking a gaseous sample from ambient air into the housing under pressure, device for sealing the environment surrounding the sensing element so that the environment surrounding the sensing element can be isolated from ambient air and evacuated, an outlet port connected to a vacuum pump for removing the gaseous sample from the environment surrounding the sensing element, wherein the size and orientation of the inlet port are selected so that the gaseous sample is directed to strike the sensing element in a turbulent flow that is substantially perpendicular to the surface having the chemoselective material, a scrubber for removing the analyte, and a structure for restoring baseline condition of the sensing element.

2. An apparatus for detecting the presence of an analyte in ambient air, the apparatus comprising a sensing element comprising a surface having a coating of chemoselective material that selectively interacts with the analyte and means to detect the selective interaction of the chemoselective material with the analyte, a housing that encloses an environment surrounding the sensing element, the housing including an inlet port connected to a sampling pump for taking a gaseous sample from ambient air into the housing under pressure, device for sealing the environment surrounding the sensing element so that the environment surrounding the sensing element can be isolated from ambient air and evacuated, an outlet port connected to a vacuum pump for removing the gaseous sample from the environment surrounding the sensing element, wherein the size and orientation of the inlet port are selected so that the gaseous sample is directed to strike the sensing element in a turbulent flow that is substantially perpendicular to the surface having the chemoselective material, wherein the inlet port includes a tubular passageway having a direction that is substantially perpendicular to the surface of the sensing element and terminates in an opening that is spaced apart from the surface of the sensing element, so that a gaseous sample passing through the inlet port is propelled onto the surface of the sensing element in a turbulent flow; wherein the outlet port comprises an annular cavity; and wherein the chemoselective material is a chemoselective polymer.

3. An apparatus for detecting the presence of at least one analyte in ambient air, the apparatus comprising (a) at least one sensing element comprising a surface having at least one coating of chemoselective material that selectively interacts with the at least one analyte and means to detect the selective interaction of the at least one chemoselective material with the at least one analyte, a housing that encloses an environment surrounding the at least one sensing element, the housing including an inlet port connected to a sampling pump for taking a gaseous sample from ambient air into the housing under pressure, means for sealing the environment surrounding the sensing element so that the environment surrounding the at least one sensing element can be isolated from ambient air and evacuated, and an outlet port connected to a vacuum pump for removing the gaseous sample from the environment surrounding the at least one sensing element, wherein the size and orientation of the inlet port are selected so that the gaseous sample is directed to strike each at least one sensing element in a turbulent flow that is substantially perpendicular to the surface of the sensing element having the chemoselective material, and (b) a fast signal kinetic chemical detector, wherein the at least one sensing element of (a) and the ion mobility spectrometer of (b) both produce a signal response and wherein the apparatus includes means to merge and simultaneously analyze the signal response of the at least one sensing element of (a) and the detector of (b).

4. An apparatus for detecting presence of an analyte in ambient air which does not require a warm-up period comprising a first valve for allowing entry/blocking of the ambient air that may contain the analyte, a sensing element having a chemoselective material on its surface for selectively interacting with the analyte, a sensor for detecting the interaction of said sensing element with the analyte, a housing that encloses environment surrounding said sensing element, an inlet port associated with said housing for passing the sample against said sensing element, the size and orientation of said inlet port are selected so that the air is directed to strike said sensing element in a turbulent flow that is substantially perpendicular to said sensing element, a device for sealing the environment surrounding said sensing element so that the environment surrounding said sensing element can be isolated from the air and evacuated, an outlet port for passing the air from the environment surrounding said sensing element, a pump connected to said outlet port for drawing the air in against the sensing element, a scrubber for removing the analyte, and a structure for restoring baseline condition of the sensing element, wherein said sensing element is about 0.3"× 0.05", said sensing element is disposed about 0.1" from said inlet port, said inlet port is about 0.4" in diameter, and the air is directed substantially perpendicularly at said sensing element at a flow rate sufficient to obtain turbulent flow.

5. An apparatus for detecting presence of an analyte in ambient air which does not require a warm-up period comprising a first valve for allowing entry/blocking of the ambient air that may contain the analyte, a sensing element having a chemoselective material on its surface for selectively interacting with the analyte, a sensor for detecting the interaction of said sensing element with the analyte, a housing that encloses environment surrounding said sensing element, an inlet port associated with said housing for passing the sample against said sensing element, the size and orientation of said inlet port are selected so that the air is directed to strike said sensing element in a turbulent flow that is substantially perpendicular to said sensing element, a device for sealing the environment surrounding said sensing element so that the environment surrounding said sensing element can be isolated from the air and evacuated, an outlet port for passing the air from the environment surrounding said sensing element, and a pump connected to said outlet port for drawing the air in against the sensing element, wherein said first valve is a 3-way valve; wherein said inlet port is tubular and is dispose substantially perpendicularly to said sensing element; and said pump is a vacuum pump.

6. An apparatus for detecting presence of an analyte in ambient air which does not require a warm-up period comprising a first valve for allowing entry/blocking of the ambient air that may contain the analyte, a sensing element having a chemoselective material on its surface for selectively interacting with the analyte, a sensor for detecting the interaction of said sensing element with the analyte, a housing that encloses environment surrounding said sensing element, an inlet port associated with said housing for passing the sample against said sensing element, the size and orientation of said inlet fort are selected so that the air is directed to strike said sensing element in a turbulent flow that is substantially perpendicular to said sensing element, a device for sealing the environment surrounding said sensing element so that the environment surrounding said sensing element can be isolated from the air and evacuated, an outlet port for passing the air from the environment surrounding said sensing element, a pump connected to said outlet port for drawing the air in against the sensing element, a scrubber in concert with said pump for removing the analyte from the air to yield a scrubbed air; and a third valve connected to said scrubber providing the scrubbed air to said sensing element.

7. An apparatus for detecting presence of an analyte in ambient air which does not require a warm-up period comprising a first valve for allowing entry/blocking of the ambient air that may contain the analyte, a sensing element having a chemoselective material on its surface for selectively interacting with the analyte, a sensor for detecting the interaction of said sensing element with the analyte, a housing that encloses environment surrounding said sensing element, an inlet port associated with said housing for passing the sample against said sensing element, the size and orientation of said inlet port are selected so that the air is directed to strike said sensing element in a turbulent flow that is substantially perpendicular to said sensing element, a device for sealing the environment surrounding said sensing element so that the environment surrounding said sensing element can be isolated from the air and evacuated, an outlet port for passing the air from the environment surrounding said sensing element, a pump connected to said outlet port for drawing the air in against the sensing element, and a fourth valve connected between said pump and said scrubber.

8. The apparatus of claim 7 including a second valve between said third and said first valves.

9. The apparatus of claim 8 wherein said first valve is a 3-way valve, said second valve is a 2-way valve, said third valve is a 2-way valve, said fourth valve is a 3-way valve, and wherein size of said pump is such as to produce flow rate of about 7 l/min.

10. The apparatus of claim 8 wherein said inlet port is tubular and is disposed substantially perpendicularly to said sensing element, and said pump is a vacuum pump.

11. The apparatus of claim 10 wherein said sensing element is about 0.3×0.05", said sensing element is disposed about 0.1" from said inlet port, said inlet port is about 0.4" in diameter, and the air is directed substantially perpendicularly at said sensing element at a flow rate sufficient to obtain turbulent flow.

* * * * *